United States Patent
Groll et al.

(10) Patent No.: US 6,280,192 B1
(45) Date of Patent: Aug. 28, 2001

(54) DEVICE FOR HANDLING DENTAL IMPLANTS

(75) Inventors: Werner Groll, Alzenau; Egbert Kremer, Hanau, both of (DE)

(73) Assignee: Degussa AG, Düsseldorf (DE)

( * ) Notice: Subject to any disclaimer, the term of this patent is extended or adjusted under 35 U.S.C. 154(b) by 0 days.

(21) Appl. No.: 09/534,298

(22) Filed: Mar. 23, 2000

(30) Foreign Application Priority Data

Mar. 24, 1999 (DE) .............................. 199 13 158

(51) Int. Cl.[7] .................................. A61C 8/00
(52) U.S. Cl. ............................. 433/173; 206/63.5
(58) Field of Search .................... 433/173, 174, 433/175, 172, 141; 206/438, 63.5

(56) References Cited

U.S. PATENT DOCUMENTS

| | | | |
|---|---|---|---|
| 4,856,648 | * 8/1989 | Krueger | 206/63.5 |
| 5,538,428 | * 7/1996 | Staubli | 433/173 |
| 5,636,990 | * 6/1997 | Stemmann | 433/189 |
| 5,692,904 | * 12/1997 | Beaty et al. | 433/141 |
| 5,951,287 | * 9/1999 | Hawkinson | 433/173 |
| 5,961,330 | * 10/1999 | Hanson | 433/173 |
| 5,964,591 | * 10/1999 | Beaty et al. | 433/173 |
| 6,083,004 | * 7/2000 | Misch et al. | 433/173 |

* cited by examiner

Primary Examiner—John J. Wilson
Assistant Examiner—Melba Bumgarner
(74) Attorney, Agent, or Firm—Smith, Gambrell & Russell, LLP

(57) ABSTRACT

A device for handling dental implants (1) with a locking screw (4). The device includes an adapter (6), which is secured to the implant (1) by a central screw (8). A ratchet insert (23) can be snap-connected to the adapter (6) in a positive-locking manner. A screwdriver (31) rotatably arranged in the ratchet insert (23), can release a screw (8) connecting the adapter (6) to the implant (1). The implant (1) connected to the adapter (6) is held by a two-part holding hub (11) in a receptacle. The implant (1) is handled by the ratchet insert (23) and is screwed into the prepared bore in the jaw.

3 Claims, 2 Drawing Sheets

DEVICE FOR HANDLING DENTAL IMPLANTS

INTRODUCTION AND BACKGROUND

The present invention relates to a method and device for handling dental implants, which comprises a locking screw provided with a threaded bore and at least one driving element on the end face, with a detachable support hub holding the implant in a receptacle and a ratchet insert which can be detachably and non-rotatably connected to the implant.

Dental implants are used in dentistry in prepared bores in the jaw. After releasing the locking screw, a sulcus molder is firstly screwed into the threaded bore of the implant followed by a post, which supports the false tooth.

The removal of the implant from its receptacle and the insertion of the implant must take place under sterile conditions. Usually, the implant is connected to a support hub, which is fitted into a tube. This tube is packed in a sterile manner in a glass bottle sealed with a lid. After opening the lid of the glass bottle, the inner tube is withdrawn together with the implant, the tube is removed and the implant is fitted into a fitting block, in which it is held in a non-rotatable manner. The support hub is then unscrewed from the implant and a ratchet insert is secured to the implant by screwing a screw extending through a central bore of the ratchet insert into the threaded bore of the locking screw of the implant.

On its end face, the ratchet insert includes projections, which engage in the driving grooves forming driving elements on the end face of the implant, so that a non-rotational connection is produced between the ratchet insert and the implant. The screwing of the implant into the prepared bore in the jaw is effected by means of a ratchet key acting upon the ratchet insert. Subsequently, the ratchet insert is unscrewed from the implant.

During the required insertion of the implant into the fitting block, the release of the support hub and the screwing in place of the ratchet insert, there is a danger of the implant becoming contaminated if the handling is not effected very carefully. In addition, this handling is associated with a considerable time expenditure.

It is therefore an object of the present invention to design a device of the initially stated type for handling dental implants in such a manner that the handling can be effected substantially more easily and reliably, so that it is also easier to maintain the sterile conditions.

SUMMARY OF THE INVENTION

The above and other objects can be attained according to the invention in that an adapter is secured to the implant by means of a central screw screwed into the threaded bore of the locking screw and engages in a positive-locking manner in the driving element of the implant, in that the adapter can be snap-connected to the ratchet insert in a positive-locking manner and in that a screwdriver is rotatably arranged in the ratchet insert so as to engage the central screw.

In this manner, it is possible to connect the implant which is already connected to the adapter in the receptacle with the ratchet insert, so long as the implant is still located in the tube and is therefore protected against accidental contamination. Following removal of the tube, the implant can be handled by means of the ratchet insert and can be screwed into the jaw by means of the ratchet key acting upon the ratchet insert. There is no need for interim depositing on a fitting block.

The connection between the ratchet insert and the adapter supporting the implant is produced in a very simple manner by snapping the ratchet insert into place after pushing over the adapter. Once the implant has been screwed into the jaw, the adapter can be easily released from the implant in that the screwdriver, which is rotatably arranged in the ratchet insert, releases the central screw screwed into the threaded bore of the locking screw.

According to a preferred embodiment of the invention, it is provided that the adapter comprises an external polygonal key profile, over which a matching internal key profile of the ratchet insert engages. In this manner, it is ensured that the relatively high torque required to screw in the implant can be reliably transmitted to the implant.

It is preferably provided that the adapter includes at least one locking recess on its external key profile, into which a resilient locking element of the ratchet insert can snap-lock. The resilient locking element can be formed by a spring ring, which partially projects into the internal key profile of the ratchet insert. In this manner, a locking connection is obtained between the ratchet insert and the adapter supporting the implant in a simple and space-saving manner in respect of the manufacturing technology involved, so that reliable handling is ensured.

The support hub is preferably formed by two half shells; an external retaining projection of the adapter engages in a retaining recess of at least one of the half shells. Consequently, it is very easy to remove the support hub following withdrawal of the implant from the tube.

BRIEF DESCRIPTION OF THE DRAWINGS

The invention will be further understood with reference to the accompanying drawings, wherein.

DETAILED DESCRIPTION OF INVENTION

Figure 1:
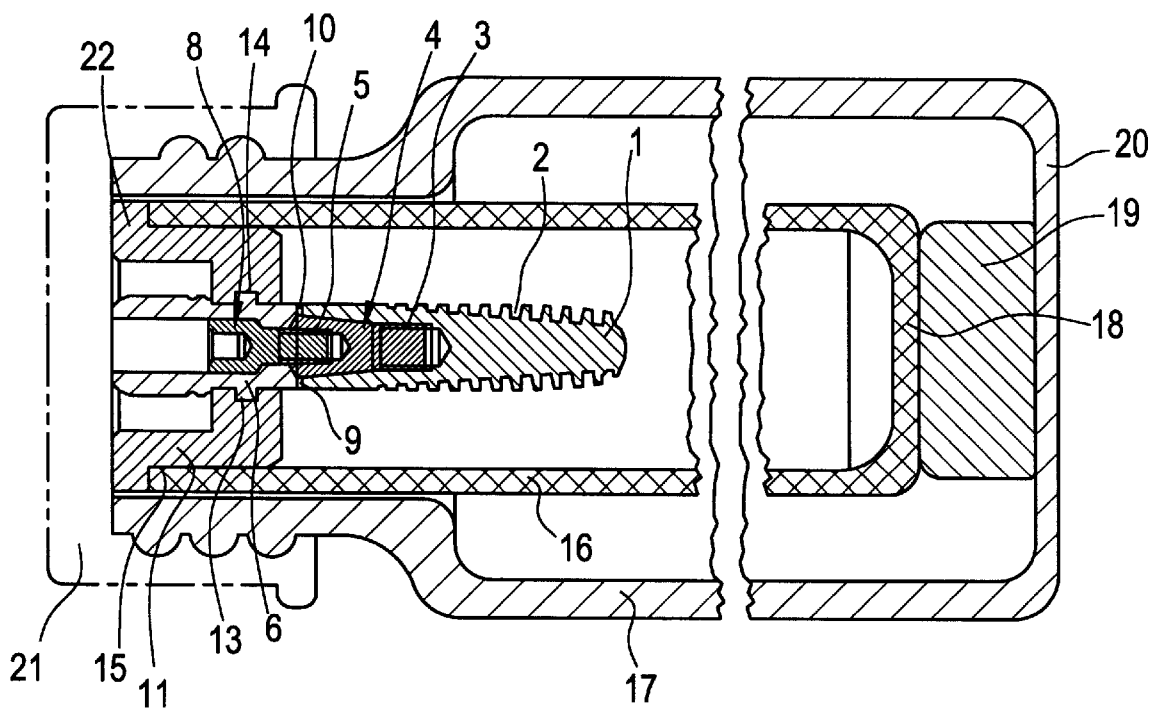
FIG. 1 is a longitudinal sectional view through an implant accommodated in a glass bottle.

The present invention will be described in further detail. A dental implant 1 comprises an external thread 2 for screwing into a human jaw and a threaded bore 3, into which a locking screw 4 is screwed. The locking screw 4 comprises a threaded bore 5.

Figure 4:
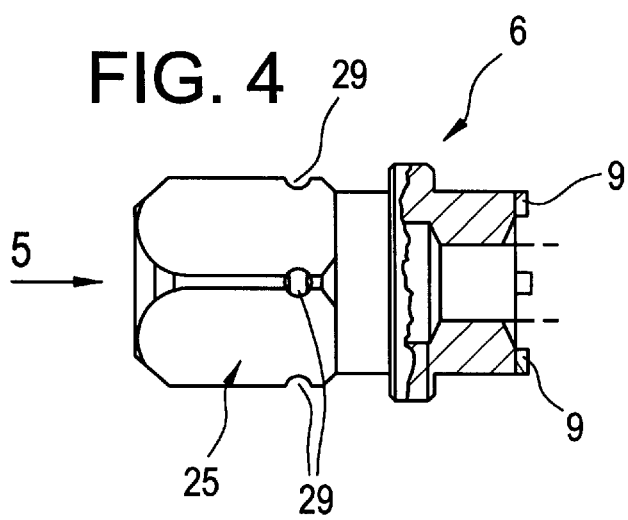
FIG. 4 is a view and partial section through the adapter connected to the implant in FIGS. 1 to 3.
Figure 5:
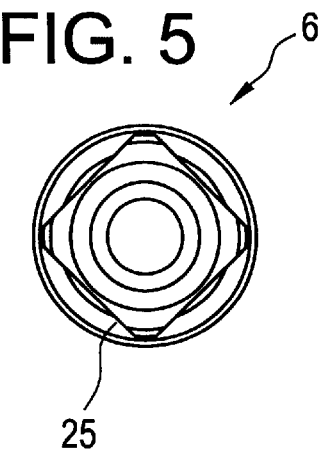
FIG. 5 is a plan view in the direction of the arrow V in FIG. 4.

A substantially sleeve-shaped adapter 6 (FIGS. 4 and 5) is screwed onto the end face of the implant 1. Arranged in a central bore 7 of the adapter 6 is a central screw 8, which is screwed into the threaded bore 5 of the locking screw 4.

As shown in FIG. 1, strips 9 (FIG. 4) projecting on the end face of the adapter 6 engage in driving grooves 10 on the end face of the implant 1 and form a non-rotatable, positive-locking connection between the adapter 6 and the implant 1. Instead of this connection, it is also possible to provide another positive-locking, non-rotatable connection between the adapter 6 and the implant 1.

Figure 6:
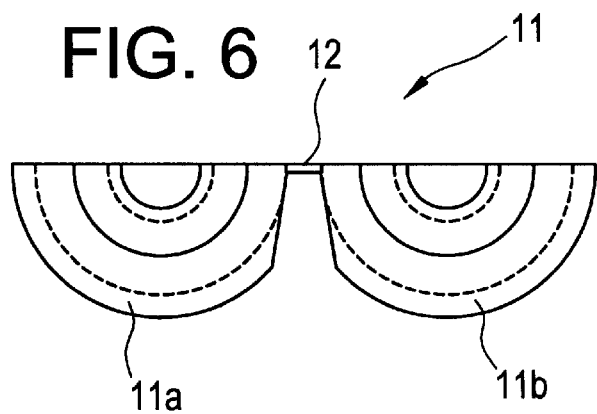
FIG. 6 shows the holding hub released from the adapter and unfolded.

A support hub 11, which is formed by two half shells 11a, 11b made of plastics material, which are connected with one another by a film hinge 12 so that they can be unfolded (FIG. 6), is engaged around the adapter 6. An external collar 13 of the adapter forms an external retaining projection, which is engaged in a circumferential inner groove 14 of the two half shells 11a, 11b.

The holding hub 11 formed by the two half shells 11a, 11b (FIG. 6) is inserted with a cylindrical external surface 15 into a cylindrical inner tube 16, which is in turn fitted into a glass bottle 17 (FIG. 1). The glass tube 16 is sealed at one end by a base 18 and is resiliently supported on the base 20 of the bottle 17 via an elastic element 19. The bottle 17 is sealed by a screw cap 21, which is only indicated in FIG. 1 by dot-dash lines, and forms a receptacle, in which the implant 1 is packed in a sterile manner and kept ready for use.

The elastic element 19 or another resilient element compensates length deviations resulting from tolerances and provides reliable holding of the tube 16 and the implant 1 in the bottle 17. The holding hub 11 formed by the two half shells 11a, 11b comprises a collar 22, which projects from the cylindrical outer surface of the holding hub 11 and is received between the open end of the tube 16 and the inner surface of the screw cap 21.

Prior to implantation, the glass bottle is opened and the sterile implant is tipped out together with the sterile tube in the sterile operating environment. The implant 1 is grasped by means of a ratchet insert 23 (FIG. 2) and is withdrawn from the tube 16. On its outer surface, the ratchet insert 23 comprises profiling 24, which is suitable for the attachment of a ratchet key (not shown). The ratchet insert 23 can be snap-connected in a positive-locking manner with the adapter 6. To this end, the adapter (FIGS. 4 and 5) comprises an external polygon key profile, in the illustrated embodiment a square profile (25), over which a matching internal key profile 26 engages. A spring ring 27 engaging around the end of the ratchet insert 23 facing the implant projects in each case in the region of the corners of the square key profile into the inner recess 28 of the ratchet insert 23 where it engages in a resilient and snap-locking manner in locking recesses 29 on the edges of the square key profile 25 of the adapter 6.

A screwdriver 31 is rotatably mounted in a central bore 30 of the ratchet insert 23. The central screw 8 screwed into the threaded bore 5 of the locking screw 4 comprises, in its screw head, a polygonal recess 32, for example a square recess, in which a matching polygonal journal 33 on the end of the screwdriver 31 facing the implant engages. At its other end projecting out of the ratchet insert 23, the screwdriver 31 is provided with a key attachment 34.

Figure 2:
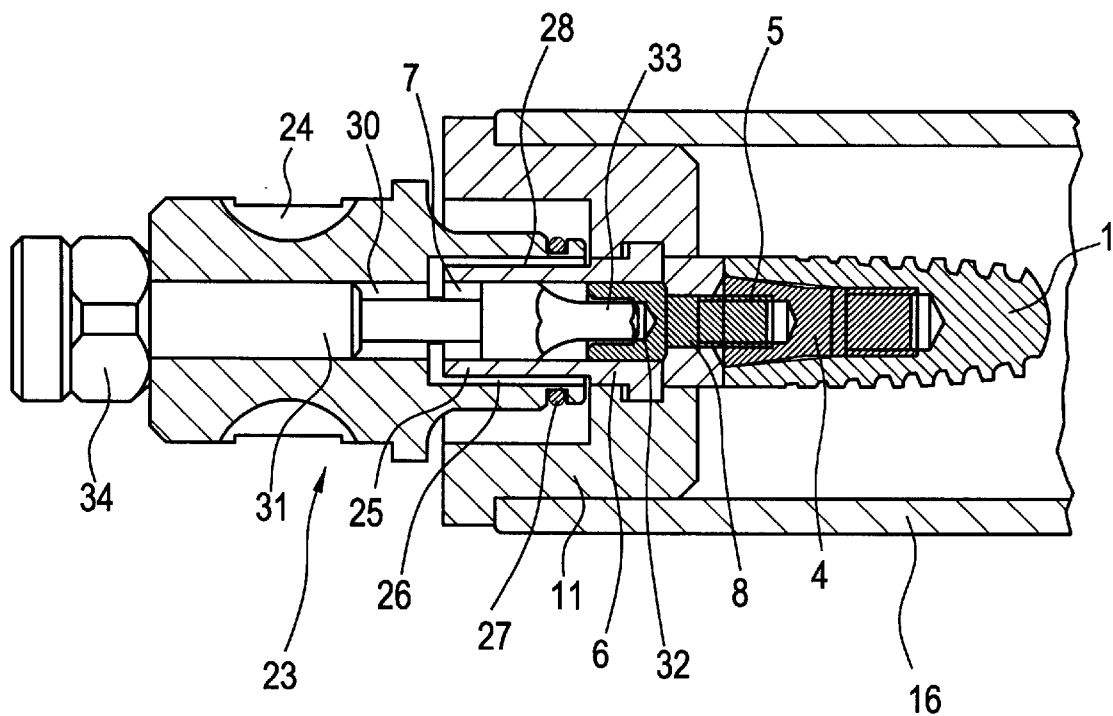
FIG. 2 is an enlarged partial longitudinal sectional view through the implant according to FIG. 1 following connection to a ratchet insert and removal from the glass bottle.
Figure 3:
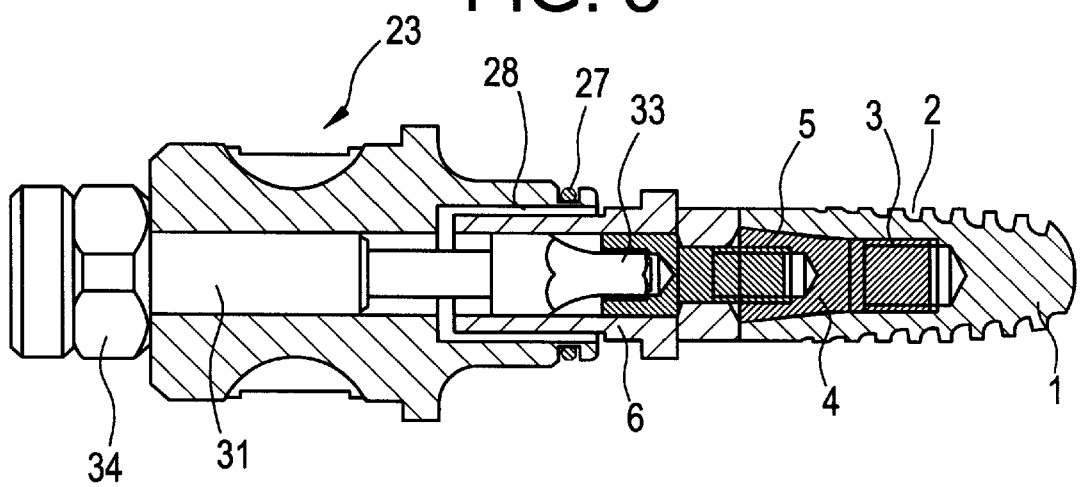
FIG. 3 shows the implant held by the ratchet insert.

Once the ratchet insert 23 has been pushed onto the adapter 6 in the snap-locking manner as shown in FIG. 2, the tube 16 is removed from the holding hub 11, which as a result of its divided design falls off the adapter 6. Using the ratchet insert 23, the operator can insert the implant 1 into the specially prepared bore in the jaw and can screw the implant into position using the ratchet key fitted onto the ratchet insert 23. Subsequently, the screwdriver 31 is rotated by means of a key fitted onto the key attachment 34 and releases the central screw 8 from the locking screw 4. The adapter 6 is thereby released from the implant 1.

Further variations and modifications of the foregoing will be apparent to those skilled in the art and are intended to be encompassed by the claims appended hereto.

German priority application 199 13 158.9 is relied on and incorporated herein by reference.

We claim:

1. A system for handling dental implants, said implants including a locking screw having a threaded bore, said system comprising:
   an adaptor secured to an implant through a threaded bore in a positive-locking manner; and
   a receptacle including a container and a closure for retaining said implant in a sterile condition and where the closure is for receiving and holding said adaptor so that said adaptor extends partially outside said receptacle;
   wherein said closure is a detachable support hub formed by two half shells with a recess for engaging said adaptor, being engagable by a tool so that said adaptor and said implant can be withdrawn from the receptacle with no contact to the implant.

2. A system according to claim 1, wherein said adaptor has an external retaining projection which engages said recess of the two half shells.

3. The system according to claim 1, wherein said two half shells are made of plastic material and connected to each other by a film hinge, so that said two half shells are foldable.

* * * * *